United States Patent [19]
Plummer et al.

[11] Patent Number: 6,114,701
[45] Date of Patent: Sep. 5, 2000

[54] CONFIGURABLE MULTIPLE DETECTOR NUCLEAR MEDICINE GANTRY

[75] Inventors: Steven J. Plummer, Hudson; Jacin C. Barnes, Willowick, both of Ohio

[73] Assignee: Picker International, Inc., New York, N.Y.

[21] Appl. No.: 09/360,898

[22] Filed: Jul. 26, 1999

Related U.S. Application Data

[60] Continuation of application No. 09/074,236, May 7, 1998, Pat. No. 5,929,446, which is a division of application No. 08/757,874, Nov. 27, 1996, Pat. No. 5,838,009.

[51] Int. Cl.[7] .................................................. G01T 1/166
[52] U.S. Cl. ............................... 250/363.05; 250/363.04
[58] Field of Search ........................... 250/363.05, 363.04

[56] References Cited

U.S. PATENT DOCUMENTS

| | | |
|---|---|---|
| 4,213,054 | 7/1980 | Doherty . |
| 4,409,484 | 10/1983 | Pinkstaff . |
| 4,649,277 | 3/1987 | Terra et al. . |
| 5,097,132 | 3/1992 | Plummer . |
| 5,206,512 | 4/1993 | Iwao . |
| 5,278,416 | 1/1994 | Pierfitte . |
| 5,349,190 | 9/1994 | Hines et al. . |
| 5,365,069 | 11/1994 | Eisen et al. . |
| 5,444,252 | 8/1995 | Hug et al. . |
| 5,523,571 | 6/1996 | Velazquez et al. . |
| 5,569,924 | 10/1996 | Plummer . |
| 5,691,538 | 11/1997 | Ohike et al. . |
| 5,717,212 | 2/1998 | Fulton et al. . |
| 5,838,009 | 11/1998 | Plummer et al. ............... 250/363.05 |
| 5,929,446 | 7/1999 | Plummer et al. ............... 250/363.05 |

FOREIGN PATENT DOCUMENTS

| | | |
|---|---|---|
| 2 697 918 | 5/1994 | France . |
| 61-83984 | 4/1986 | Japan . |

*Primary Examiner*—Constantine Hannaher
*Attorney, Agent, or Firm*—Timothy B. Gurin; John J. Fry; Eugene E. Clair

[57] ABSTRACT

A transformable gamma camera includes detectors mounted for circumferential movement with respect to a rotating gantry. The rotating gantry includes radial bores at desired angular positions about the rotating gantry. The stationary gantry includes a docking station such as a bore. A coupling mechanism allows the detectors to be coupled to the bores in the rotating gantry or to the docking station. Each of the detectors is movable radially with respect to the rotating gantry's axis of rotation and tangentially to the imaging region. The gamma camera is readily transformable between 120 degree, orthogonal, and opposed detector configurations; a plurality of aperture sizes can also be defined.

13 Claims, 9 Drawing Sheets

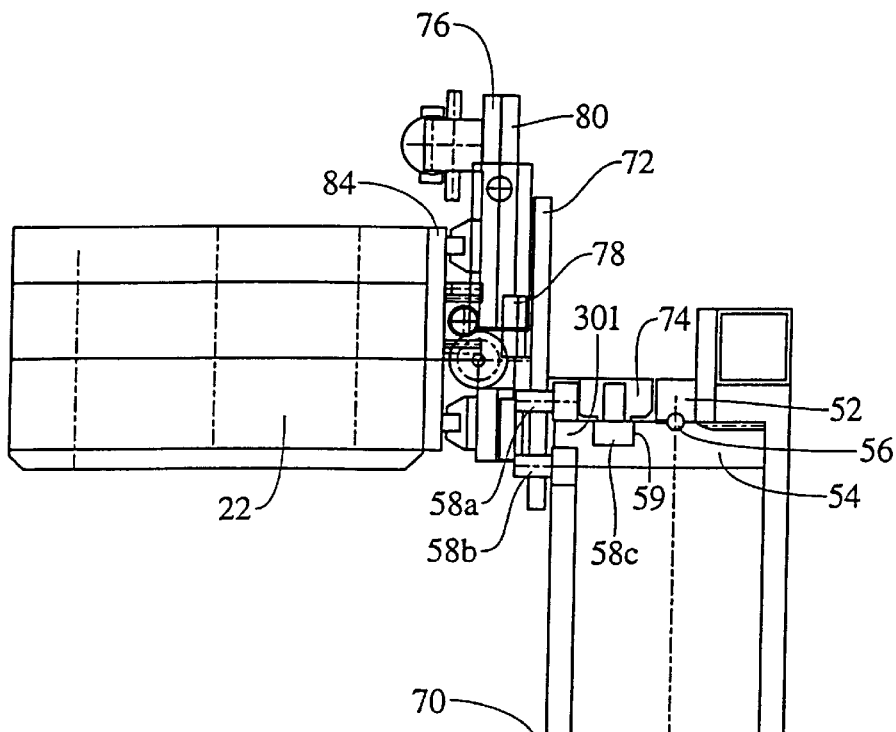
Fig. 2
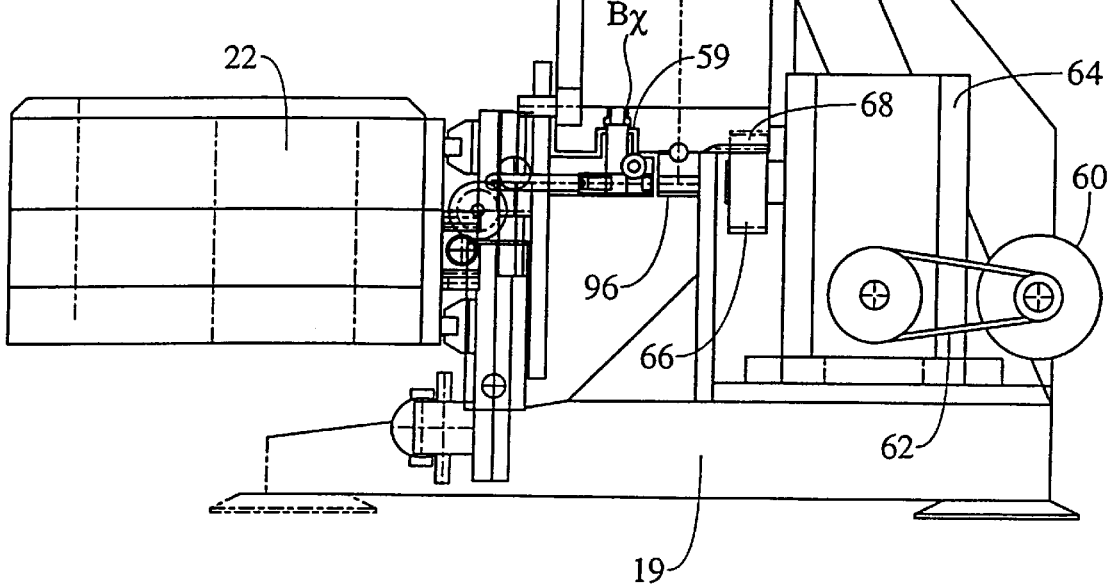

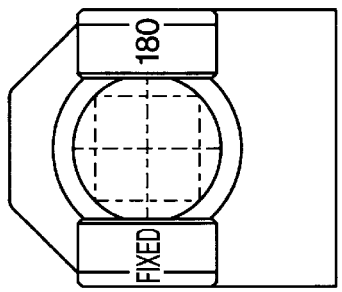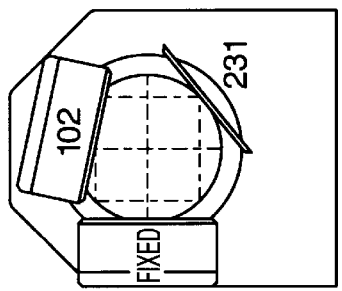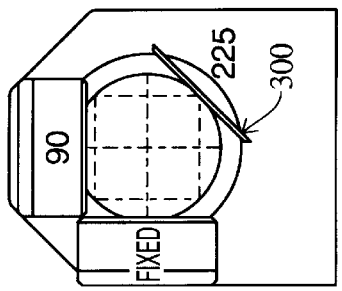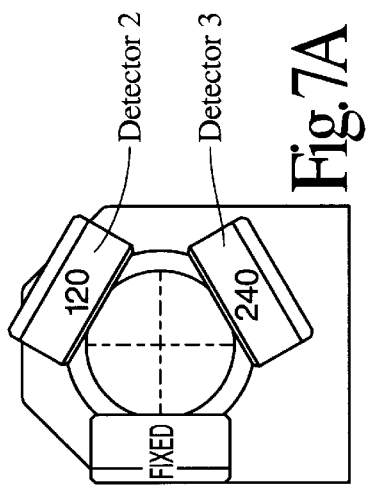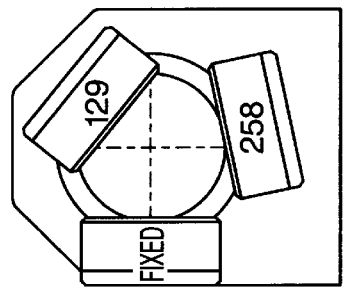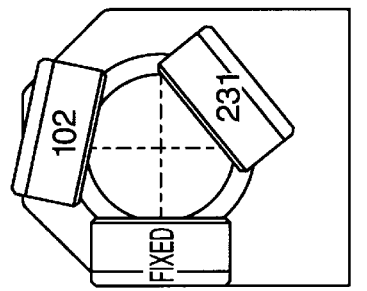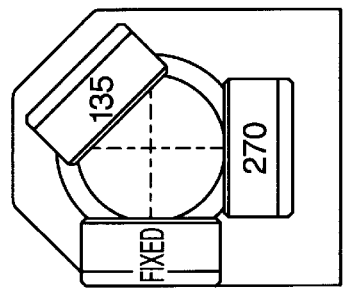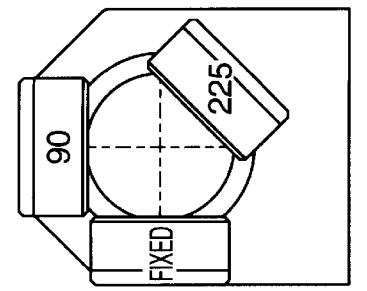

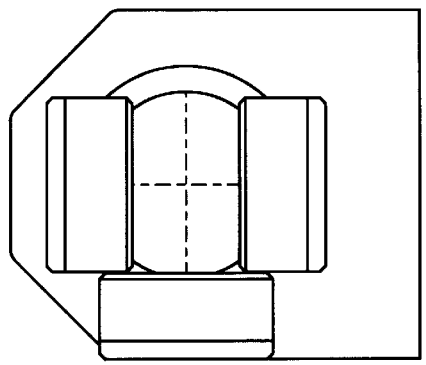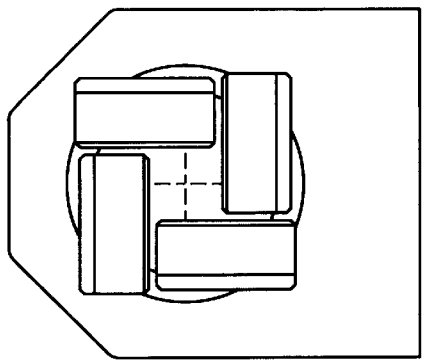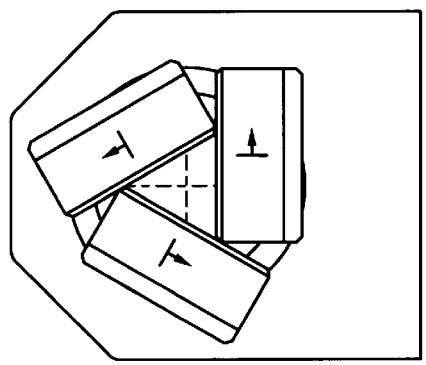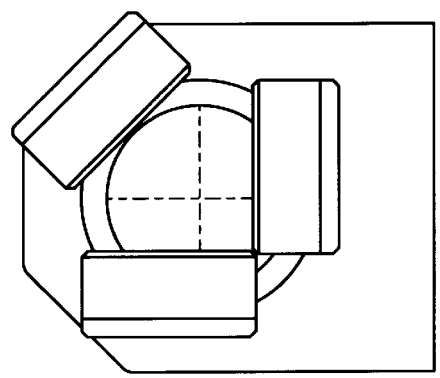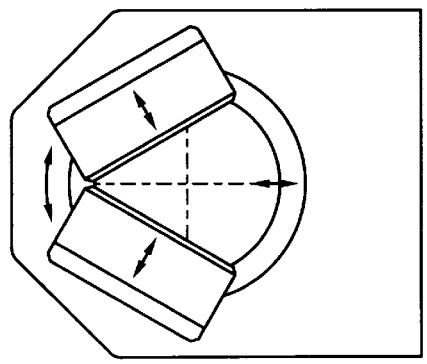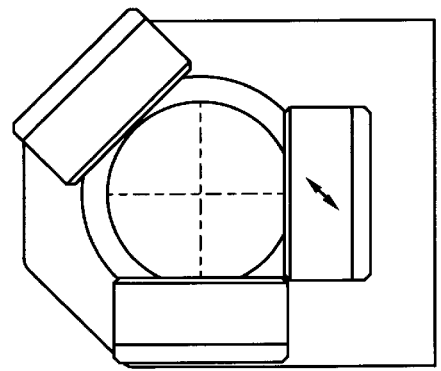

CONFIGURABLE MULTIPLE DETECTOR NUCLEAR MEDICINE GANTRY

This is a continuation of application Ser. No. 09/074,236 (filed May 7, 1998) now U.S. Pat. No. 5,929,446 (issued Jul. 27, 1999), which is a division of application Ser. No. 08/757,874 (filed Nov. 27, 1996) now U.S. Pat. No. 5,838,009 (issued Nov. 17, 1998).

BACKGROUND OF THE INVENTION

The present invention relates to the nuclear medicine art. It finds particular application in conjunction with multiple detector single photon emission computed tomography (SPECT) camera systems and will be described with particular reference thereto.

Early nuclear or Anger cameras had a single radiation detector head which was positioned stationarily over a region of interest of the subject. The subject was injected with a radioactive dye which circulated through the patient's circulatory system. Some of the radiation given off by the dye was received by the gamma camera detector head which converted the radiation event into light.

More specifically, the detector head included a scintillation plate which converted each received radiation event into a scintillation or flash of light. An array of photomultiplier tubes positioned in the back of the scintillator plate and associated circuitry determined an (x,y) coordinate location and an energy of (z) value for each scintillation event. A collimator including a grid-like array of lead vanes limited the path or trajectory of radiation events which could strike the scintillation plate. Typically, the collimator constrained each incremental element of the scintillator plate to be receptive only to radiation directly in front of it, i.e., radiation along paths substantially perpendicular to the scintillator plate. The collimator must be positioned as close to the patient as possible to acquire image data required to generate high resolution images. In this manner, a shadowgraphic image of the frequency of radiation events in the examined region of the subject was developed.

In SPECT imaging, the detector is rotated around the subject or indexed to a multiplicity of angularly offset positions around the subject to collect a data which is the mathematical equivalent of a CT scanner data set. More accurately, because the nuclear camera head is two-dimensional, a series of data sets are collected, each corresponding to one slice of an imaged volume.

Instead of a single detector head, other gamma cameras have two detector heads positioned on opposite sides of the subject. Placing two detector heads in this manner improves the resolution and data collection efficiency, particularly for whole body imaging. For other studies, particularly cardiac studies, it is advantageous to position the detector heads orthogonally to each other. This enables a complete 180 degree data set to be collected by rotating the pair of detector heads only 90 degrees relative to the subject. Still other gamma cameras have three heads placed at 120 degree intervals around the subject. Typically, the heads are movable radially toward and away from the patient and the three heads are rotatable, as a unit, around the patient. In each case, the detector face is placed as close as possible to the patient during.

Each of the foregoing systems has various advantages and disadvantages. The cost of a gamma camera system increases as additional detector heads are added. Systems having two opposed detector heads are particularly useful for whole-body imaging. Wide field of view detectors, which permit scanning of the entire width of the body, are preferably used in this application. Systems having two orthogonal detectors are commonly used for cardiac imaging. Because a wide field of view is not required in cardiac applications, smaller detectors are preferably used to allow the detectors to be placed as close as possible to the patient. Three detector head systems are often used in connection with high resolution brain and cardiac imaging. Although wide field of view detectors are desirable for body imaging, their physical size again limits performance in head imaging. The placement of the three detector heads also limits the utility of three detector systems in whole body and brain applications.

These tradeoffs limit the versatility of traditional gamma camera systems. As a result, various attempts have been made to address them.

U.S. Pat. No. 5,444,252 to Hug, et al., issued Aug. 22, 1995 discloses a two detector system whereby the detectors are transformable between opposed and orthogonal positions. A separate driven mechanism and ring gear for each of the detectors increases the cost and physical complexity of the system. The minimum distance between the detectors and the patient in the orthogonal configuration, and hence system performance, is also limited by the physical size of the detector heads.

Co-pending U.S. application Ser. No. 08/292,785 now U.S. Pat. No. 5,569,924 discloses a system having two detectors which can be transformed between opposed and orthogonal configurations. Although the physical size of the detectors continues to limit the minimum distance between the patient and the detectors in the orthogonal configuration, this effect is reduced by offsetting the detector field of view from the center of rotation. This system is not readily adapted to a three detector configuration, however.

Co-pending U.S. application Ser. No. 08/635,390 now U.S. Pat. No. 5,717,212 discloses a three detector system where two of the three heads can be independently positioned about the gantry so that 120 degree three head, 180 degree opposed, and 90 degree orthogonal configurations can all be achieved. Although the physical size of the detector again limits the minimum distance between the detectors and the patient, the distance is reduced in the 90 degree orthogonal position by varying the angle from 90 degrees. The physical size of the detectors again limits the minimum distance between the detector faces and the patient in the 120 degree configuration.

The present invention provides a gamma camera which addresses the above-referenced shortcomings, and others.

SUMMARY

According to a first aspect of the present invention, a gamma camera includes a first radiation sensitive detector for detecting radiation from an examination region. The first detector is selectively translatable in first and second directions in relation to the examination region. The gamma camera also includes a second radiation sensitive detector for detecting radiation from the examination region. The second detector is selectively translatable in first and second directions in relation to the examination region. The first and second detectors are selectively rotatable about the examination region so as to detect radiation at a plurality of angular positions thereabout. The second detector is selectively rotatable about the examination region with respect to the first detector. The first and second detectors are selectively rotatable about the examination region in at least first and second relative angular orientations.

According to a more limited aspect, the gamma camera includes a first drive for translating the first detector in the first direction, a second drive for translating the first detector in the second direction, a third drive for translating the second detector in the first direction, and a fourth drive for translating the second detector in the second direction. According to a still more limited aspect, the first drive translates the first detector in a radial direction, the second drive translates the first detector in a tangential direction, the third drive translates the second detector in the radial direction, and the fourth drive translates the second detector in the tangential direction.

According to another more limited aspect, the radiation is at least one of emission radiation and transmission radiation.

According to still another more limited aspect, the first direction is a radial direction and the second direction is a tangential direction.

According to still other more limited aspects, the first relative angular orientation may be a 120 degree orientation and the second relative angular orientation may be an orthogonal orientation. The first relative angular orientation may be a 120 degree orientation and the second relative angular orientation may be an orthogonal orientation. The first relative angular orientation may be a 180 degree orientation and the second relative angular orientation may be an orthogonal orientation. The first and second detectors may be selectively rotatable about the examination region in at least first, second, and third relative angular orientations, said third relative angular orientation being a 120 orientation.

According to another aspect of the present invention, a gamma camera includes first and second radiation sensitive detectors for detecting radiation indicative of radionuclide decays. The first and second detectors are selectively rotatable about an axis of rotation. The first detector is selectively rotatable about the examination region in relation to the second detector such that the detectors are selectively positionable in at least first and second relative angular orientations for rotation about the examination region. The gamma camera also includes a tangential drive operatively connected to the first detector, a radial drive operatively connected to the second detector, a tangential drive operatively connected to the second detector, and a radial drive means operatively connected to the second detector.

One benefit of the present invention is that the configuration of the detectors may be readily changed. For example, the detectors may be placed in opposed, orthogonal, and 120 degree configurations. As a result, a single gamma camera may be used in a variety of applications. Another benefit is that the gamma camera may be produced with one or two detectors and readily upgraded to include additional detectors.

The present invention also allows the faces of the detectors to placed near to the patient while allowing relatively large detectors to be used. This improves the image quality of the gamma camera while enhancing the camera's flexibility in multiple applications.

Still yet other benefits and advantages will be appreciated by those skilled in the art upon reading and understanding the following description.

DRAWINGS

FIG. 2 is a sectional side view of a gamma camera according to the present invention.

FIGS. 7a–7i are front views of a gantry depicting various detector configurations.

FIGS. 8a–8f are front views of a gantry depicting various detector configurations.

DESCRIPTION

Figure 1:
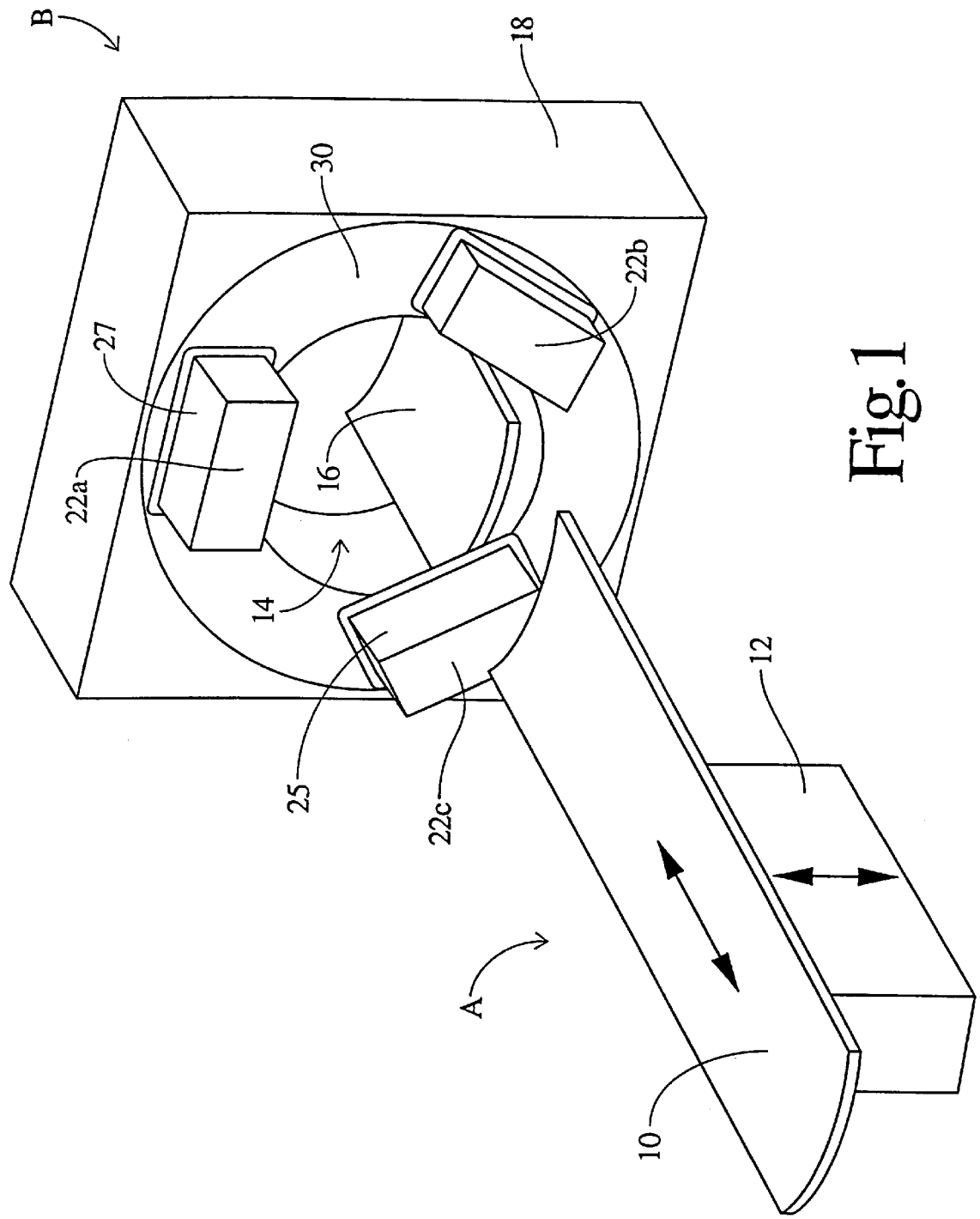
FIG. 1 is a front perspective view of a gamma camera according to the present invention.

With reference to FIG. 1, a patient is supported on a patient support A. The patient support includes a thin, relatively radiation transmissive support surface 10 which is mounted cantilevered from a base 12. The base includes motors for raising and lowering the patient support surface and for extending and retracting the support surface relative to a nuclear camera gantry B.

Figure 9:
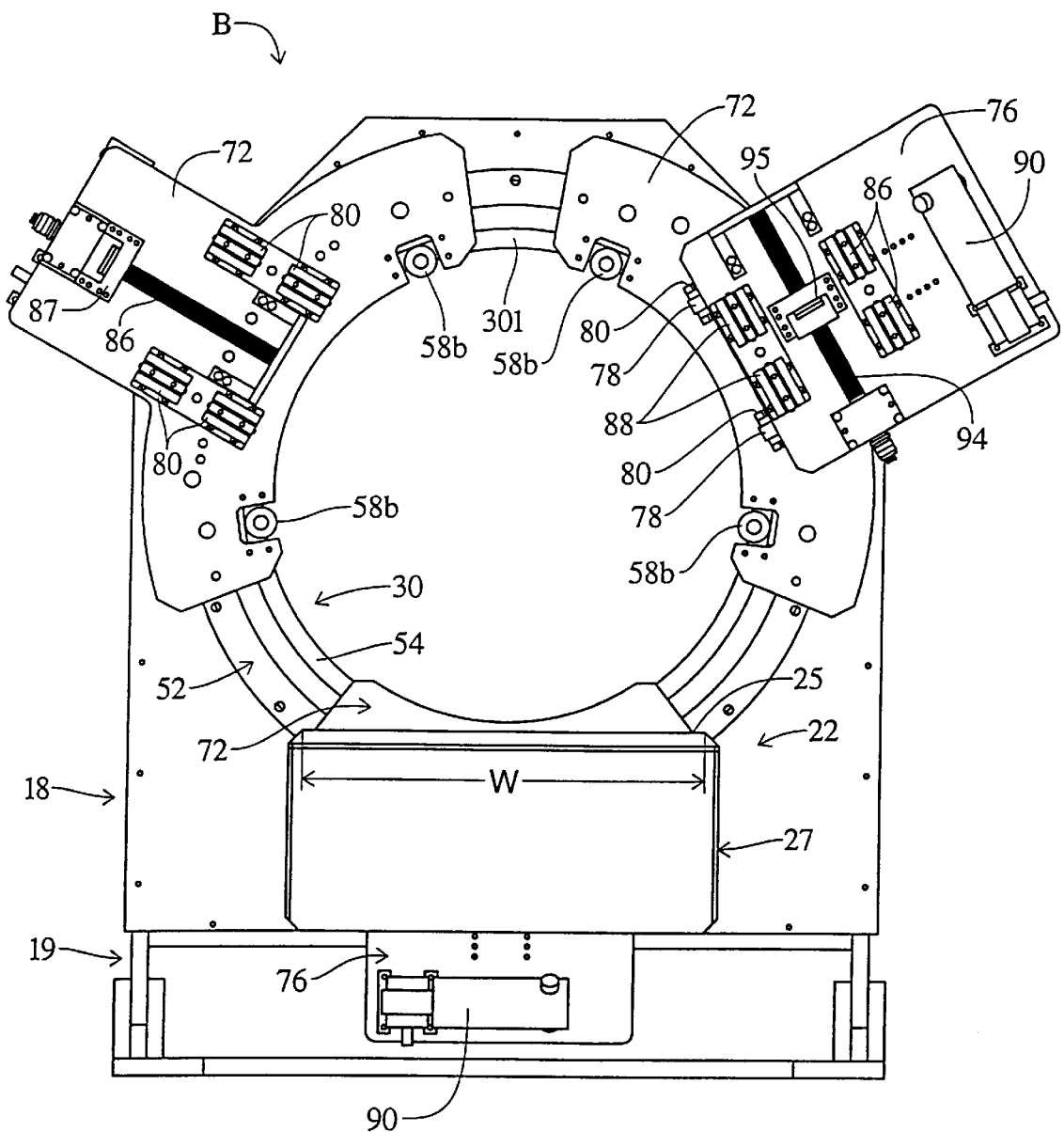
FIG. 9 is a front view of a gantry depicting the various drive mechanisms.

With reference to FIGS. 1, 2, and 9, the gantry B includes stationary 18 and rotating 30 gantry portions which are operatively connected by a bearing having an outer 52 and an inner 54 race. The stationary gantry 18 includes a support frame 19. The outer race 52 of the bearing is fastened to the frame 19.

The rotating gantry structure 30 includes the inner bearing race 54. A raceway 56 between the inner 54 and outer 52 races contains bearings which facilitate rotation of the inner race 54 about an axis of rotation 70. A rotate drive mechanism includes a rotate drive motor 60, belt 62, gearbox 64, and drive pinion 66. The drive pinion 66 engages teeth 68 disposed on the outer circumference of the inner race 54 to rotate the inner bearing race 54 and hence the rotating gantry 30.

Detectors 22a, 22b, 22c are mounted to the rotating gantry portion 30 and define an aperture into which the anatomy of a patient may be inserted. Each detector 22 has a body 27 and a face 25. Each detector is characterized by a width w. As the gantry rotates about the axis of rotation 70, the rotating detectors define a generally circular imaging region, the precise shape of which may vary if the detectors are moved radially during rotation of the gantry 30. As described below, the detectors are mounted to the gantry 30 so as to be movable angularly with respect to the rotating gantry 30, radially toward and away from the axis of rotation 70, and tangentially with respect to the imaging region.

Figure 3:
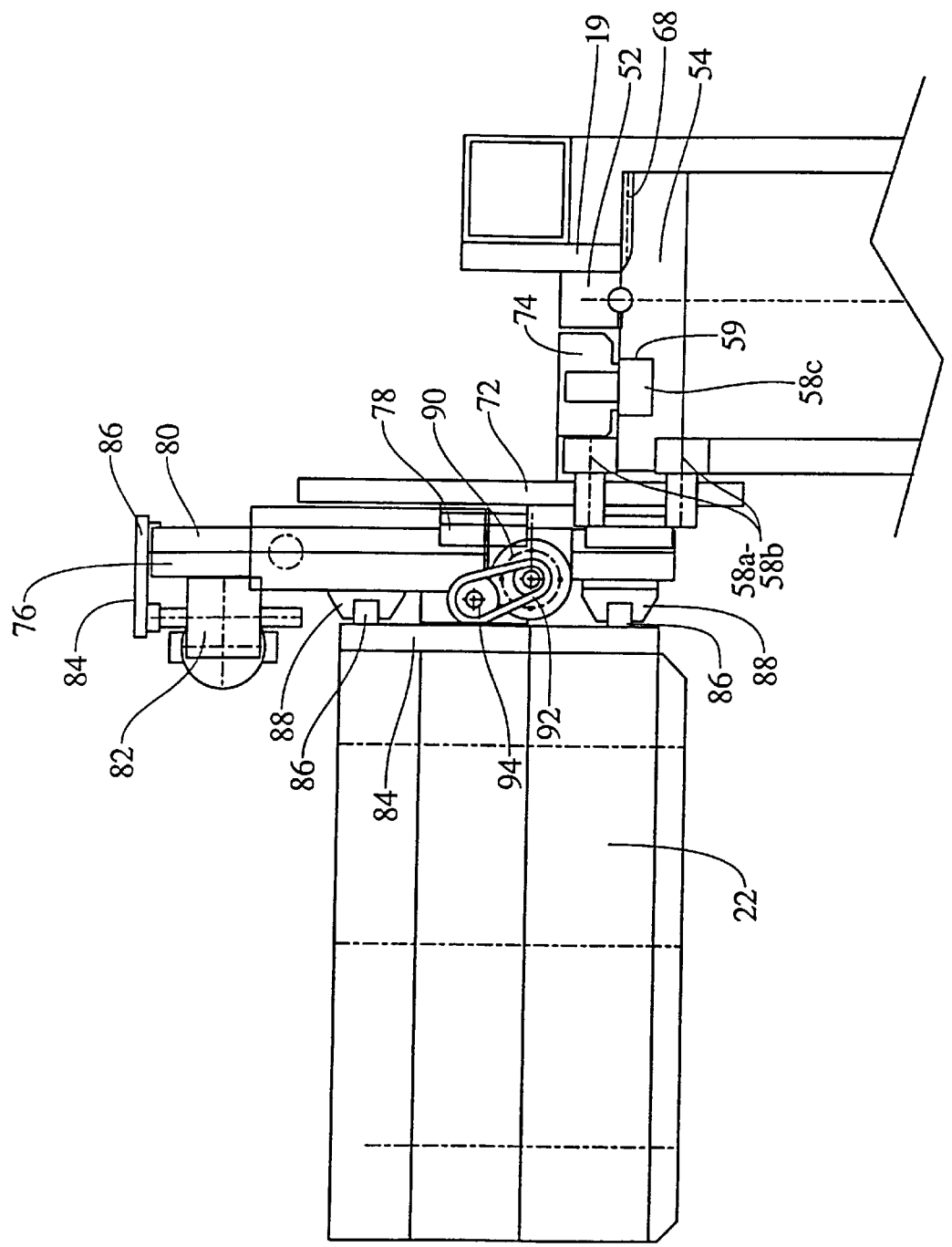
FIG. 3 is an enlarged view of the upper portion of FIG. 2.

Turning now to FIGS. 3 and 9, the inner bearing race 54 supports detector supports 72. The detector supports 72 are rotatably mounted to the inner race 54 using two sets (for a total of four) of shear load cam followers 58a, 58b and four moment load cam followers 58c at spaced angular positions on the support 72. The moment load cam followers 58c are rotatably attached to mounting blocks 74 which are in turn fastened to the detector support 72. The moment load cam followers 58c engage within a groove 59 in the outer circumference of the inner bearing race 54. The shear load cam followers 58a, 58b engage either side of a protrusion 301 on the inner race 54. This arrangement allows the inner bearing race 54 to be rotated with respect to the supports 72 and hence the detectors 22. Viewed from another perspective, the detectors may be moved circumferentially about the inner race 54 to a variety of relative angular positions.

In a gantry having three detectors 22, two of the detectors are movable circumferentially with respect to the race while the third (for example, the detector 22 shown at the bottom or 6 o'clock position in FIG. 9) is attached to the inner race at a fixed angular position. More generally, in a gantry having multiple detectors, one of the detectors is preferably attached to the inner race 52 at a fixed angular position while the remaining detectors are mounted for circumferential motion. As will be appreciated, this arrangement reduces the cost and extra structure associated with the circumferential mounting arrangement.

Radius drives move each of the detectors in direction radially toward and away from the axis of rotation 70. A radius drive support 76 is mounted to each detector support 72. A set of parallel bearing rails 78 is fastened to the radius drive support 76; corresponding bearing blocks 80 are fastened to the detector support 72. A radius drive mechanism, including radius drive gear motor 82, radius drive chain 84, radius drive screw 86, and radius drive block 87 causes the radius drive support 76 to move along the blocks 80 in the radial direction.

Tangential drives move each of the detectors in a direction tangential to the imaging region. A tangential drive support 84 is mounted to each radius drive support 76. A set of bearing rails 86 is fastened to the tangential drive support 84; corresponding bearing blocks 88 are fastened to the radius drive support 76. The tangential bearing blocks 88 and rails 86 are perpendicular to the radius bearing blocks 80 and rails 78. A tangential drive mechanism, including tangential drive gear motor 90, tangential drive chain 92, tangential drive screw 94, and tangential drive block 95 causes the tangential drive support 84 to move along the bearing blocks 88 in a direction tangential to the imaging region.

The detector 22 is fastened to the tangential drive support 84 with its face parallel to the tangential bearing rails 86 and blocks 88 and perpendicular to the radius bearing rails 78 and blocks 80.

Figure 4:
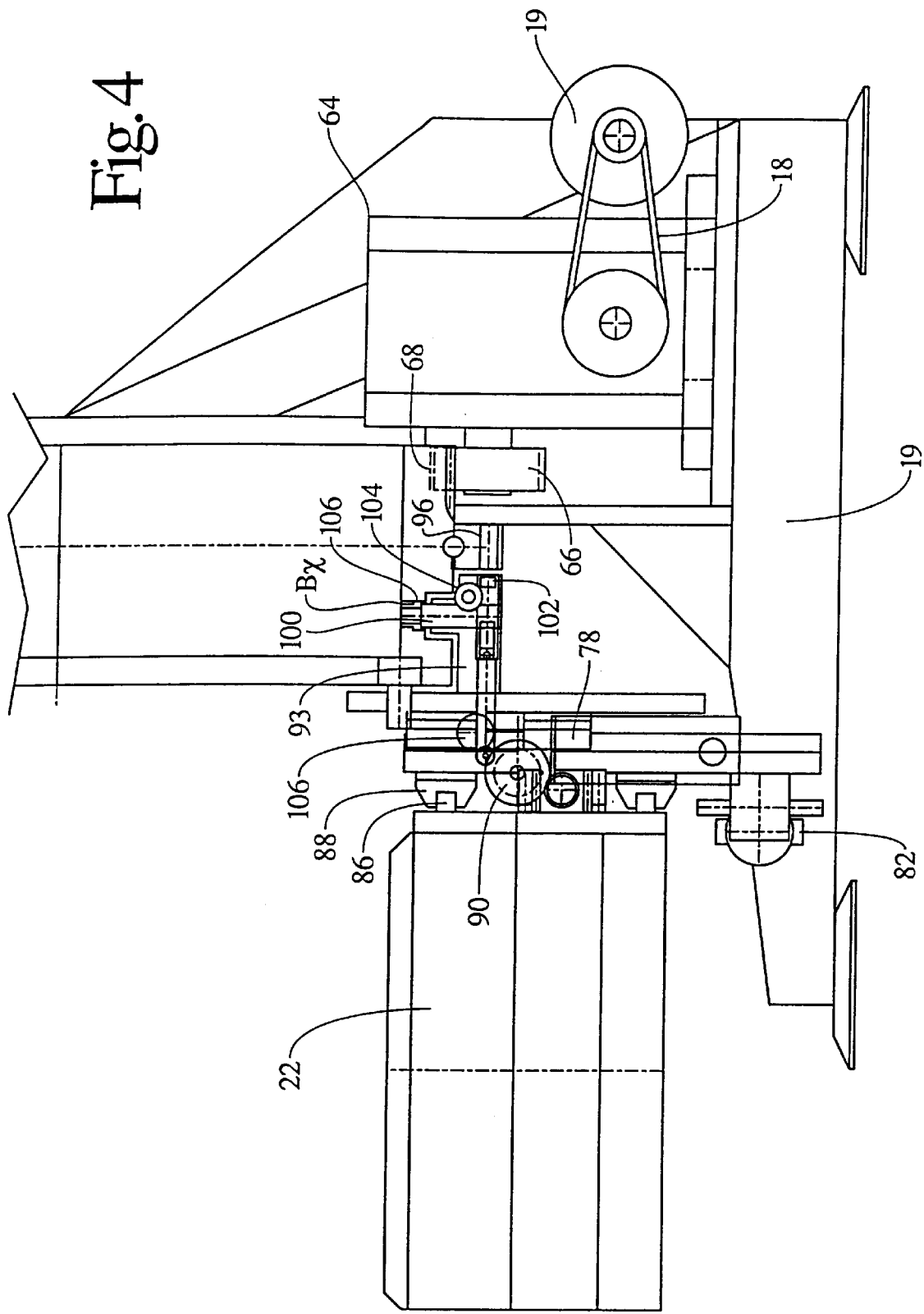
FIG. 4 is an enlarged view of the lower portion of FIG. 2.
Figure 5:
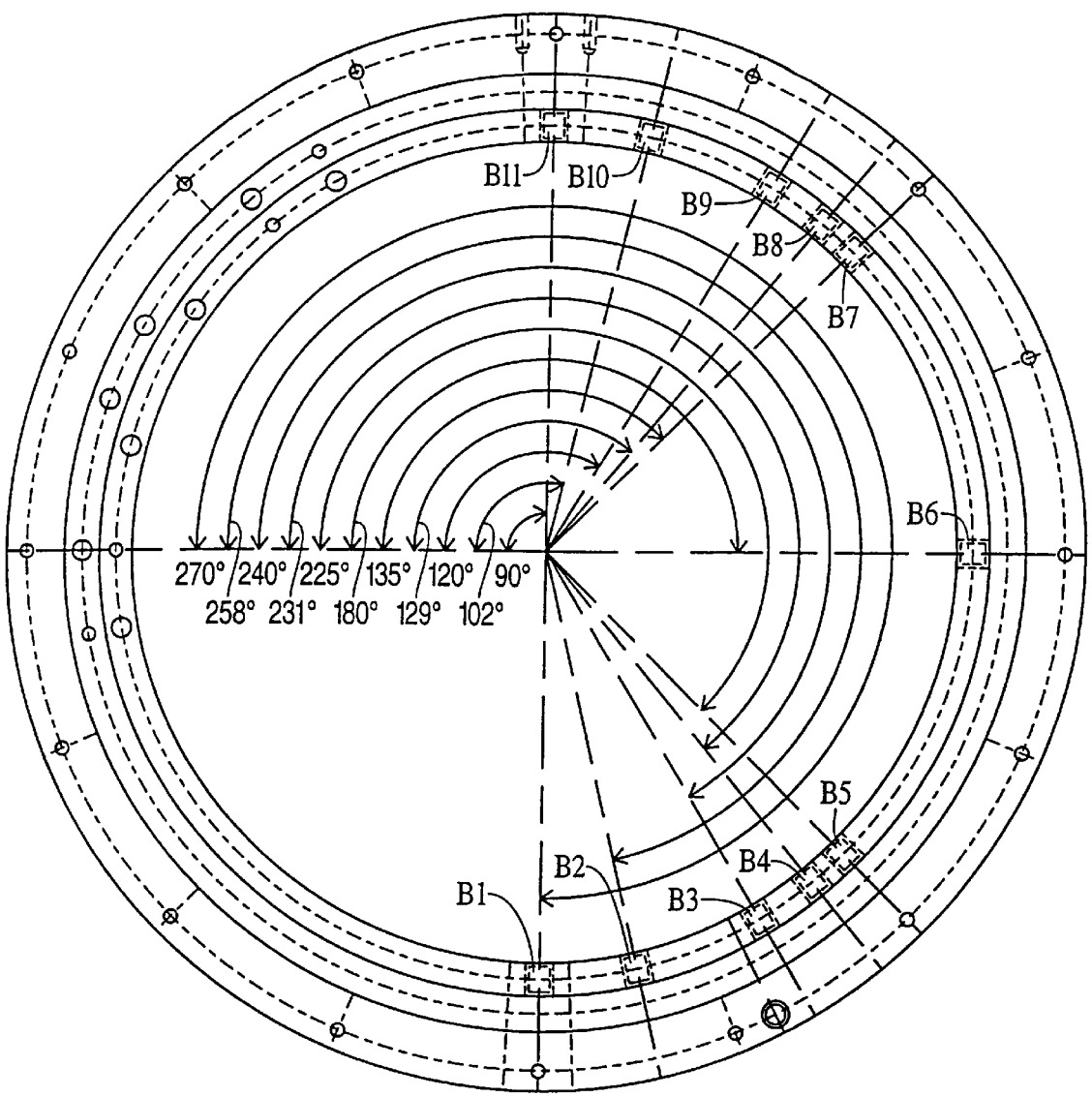
FIG. 5 is a front view of a bearing.
Figure 6:
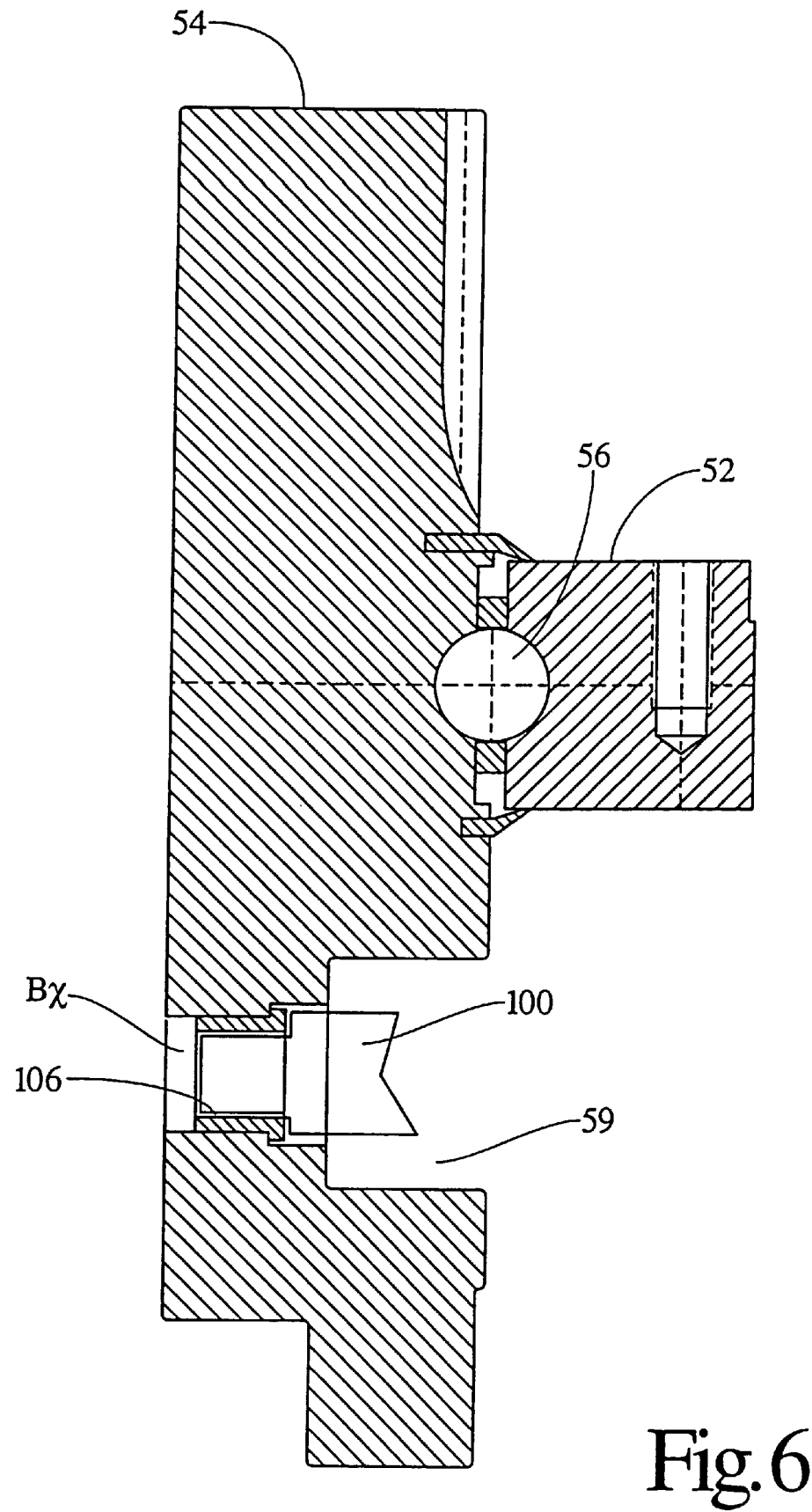
FIG. 6 is a sectional view through 6—6 of FIG. 5.

A coupling mechanism allows the detectors which are movable circumferentially with respect to the inner race 54 to be selectively coupled to the rotating gantry 30 and the stationary gantry 18. With reference to FIGS. 5 and 6, the inner bearing race 54 contains radial bores B1–B11 at various angular positions. The bores $B_x$ are contained in the inner surface of the groove 59 which supports the moment cam follower 58c. With reference to FIGS. 2 and 4, the stationary gantry portion 18 also includes a docking station such as a bore 96 disposed in the outer bearing race 52, preferably at the lowermost or 6 o'clock position.

A locking pin mounting block 98 is fastened to the detector support plate 72 of each circumferentially movable detector. The mounting block in turn supports an inner race locking pin 100 and a frame locking pin 102. The inner race locking pin 100 is movable in a radial direction to engage the radial bores $B_x$. The frame locking pin 102 is movable in a direction to engage the bore 96. The inner race locking pin 100 and the frame locking pin 102 are coupled by a pin to pin drive gear 104. A locking pin actuator 106 mounted to the detector support plate 72 is operatively connected to the frame locking pin 102. FIGS. 2 and 4 show the inner race locking pin 100 engaged in one of the radial bores $B_x$ while frame locking pin 102 is disengaged from the outer race bore 96. In this position, the detector is locked at a fixed angular position on the inner race 52.

The actuator 106 may be energized to urge the frame locking pin 102 to engage the outer race bore 96. Drive gear 104 simultaneously causes the inner race locking pin 100 to retract so that it disengages from the bore $B_x$. In the preferred embodiment, the frame locking pin 102 locks the detector assembly to the outer race 52 before the inner race locking pin 100 disengages from the inner race 54. Similarly, the inner frame locking pin 100 preferably engages the bore $B_x$ before the frame locking pin 102 disengages from the outer race bore 96.

The frame locking pin 102 engages limit switches (not shown) to confirm that the frame locking pin is in the extended or the retracted positions. Proximity switches (not shown) associated with each of the inner race bores $B_x$ confirm whether an inner race locking pin is engaged therein. With reference to FIG. 5, each bore includes an insert 106 for accepting the inner race locking pin 100. The locking pin 100 has a stepped, relatively smaller cross section at its distal end. In the event that the distal end of the tip should fail, the section having the larger cos section remains engaged in the bore, thereby continuing to support the detector.

The camera is ordinarily operated with each of the detectors 22 coupled to the inner race 52 for motion with the rotating gantry. To conduct a scan, the rotate drive causes the rotating gantry and each of the detectors 22 to rotate together as a unit about the imaging region.

The configuration of the detectors may be adjusted by rotating the inner race 52 until a desired circumferentially movable detector 22 reaches the 6 o'clock position. Locking pin actuator 106 extends the frame locking pin 100 into the outer race bore 96 and retracts the inner race locking pin 100 from the bore $B_x$ to couple the detector to the docking station and free it from the rotating gantry 30. The inner race 52 is rotated to a desired position, i.e., until the inner race locking pin 100 is aligned with the desired inner race bore $B_x$. The inner race locking pin 100 is extended into the bore $B_x$; the frame locking pin 102 is retracted from the outer race bore 96 such that the detector 22 is coupled to the inner race 54 in its new angular position. This process is repeated until each of the movable detectors is placed in a desired angular position.

Examples of detector configurations are shown in FIGS. 7a–7i. Table 1 depicts the bore $B_x$ associated with each detector head for the configurations of FIG. 7. The detector configurations shown in FIG. 7 and Table 1 are not exhaustive.

TABLE 1

| Figure | Detector 2 | Detector 3 |
| --- | --- | --- |
| 7a | B9 | B3 |
| 7b | B11 | B1 |
| 7c | B11 | B5 |
| 7d | B10 | B4 |
| 7e | B7 | B1 |
| 7f | B8 | B2 |
| 7g | B11 | B5 |
| 7h | B10 | B4 |
| 7i | B6 | x |

FIGS. 7a–7f depict configurations for a three detector gantry. FIG. 7b shows a three detector gantry with two of the detectors configured in a 180 degree opposed configuration. The opposed detectors provide anterior and posterior images. The third detector produces a lateral image which provides depth information. As shown in FIGS. 7g and 7f, a transmission radiation source 300 may be substituted for one of the detectors. FIG. 7i depicts a system having two heads configured in a 180 degree opposed configuration. Of course, four or more detectors can also be accommodated. Note that FIG. 7 and Table 1 are not an exhaustive list of the possible configurations. Other desirable configurations may readily be implemented by placing bores $B_x$ in other angular positions of by using different combinations of bores $B_x$.

Similarly, the two detectors in a two detector gantry can be placed at any of the angular positions shown in FIG. 7. Thus, a two detector gantry can be configured, for example, in 180 degree opposed, 90 degree orthogonal, or 102 degree orthogonal positions.

As depicted by the radial arrows in FIG. 8a, the radial drives move the detectors 20 radially toward and away from the imaging region. As can be seen, the minimum aperture size and hence the minimum distance between the faces of the detectors and the patient is limited by the width of the detectors. The present invention permits the detectors 22 to be irised so that the minimum distance between the detector faces and the patient can be reduced from the limit otherwise defined by the detector widths. As depicted by the tangential arrows in FIG. 8b, the tangential drives permit the detectors to be moved in a direction generally tangential to the imaging region. As a result, mechanical interference between the corners of the detectors can be avoided, and the radial drives can be used to place the faces of the detectors closer to the patient. As shown in FIG. 8b, a portion of each detector face extends beyond the body of another detector. As will be appreciated, the width of each side of the aperture has a dimension smaller than the width of the corresponding detector. In this way, the detectors may be positions to define a variety of different aperture sizes. A four detector gantry is depicted in FIG. 8f.

FIGS. 8c and 8d depict a three detector gantry having two detectors arranged in a 90 degree configuration which is especially efficient for cardiac imaging. As shown in FIG. 8c, the minimum distance between the detector heads is ordinarily limited by the size of the detectors 20. Using a combination of tangential and radial motion which produces motion in the direction depicted by the arrows in FIG. 8c, however, the detectors can be positioned much nearer to the axis of rotation as shown in FIG. 8d.

The invention has been described with reference to the preferred embodiment. Obviously, modifications and alterations will occur to others upon reading and understanding the preceding description. It is intended that the invention be construed as including all such modifications and alterations insofar as they come within the scope of the appended claims or the equivalents thereof.

Having disclosed the preferred embodiment, the invention is now claimed to be:

1. A gamma camera comprising:
    a first radiation sensitive detector for detecting radiation from an examination region, wherein the first detector is selectively translatable in first and second directions in relation to the examination region;
    a second radiation sensitive detector for detecting radiation from the examination region, wherein the second detector is selectively translatable in first and second directions in relation to the examination region;
    wherein the first and second detectors are selectively rotatable about an axis of rotation so as to detect radiation at a plurality of angular positions about the examination region, the second detector being selectively rotatable about the axis of rotation with respect to the first detector, whereby the first and second detectors are selectively rotatable about the examination region in at least first and second relative angular orientations.

2. The gamma camera of claim 1 including a first drive for translating the first detector in the first direction, a second drive for translating the first detector in the second direction, a third drive for translating the second detector in the first direction, and a fourth drive for translating the second detector in the second direction.

3. The gamma camera of claim 2 wherein the first drive translates the first detector in a radial direction, the second drive translates the first detector in a tangential direction, the third drive translates the second detector in the radial direction, and the fourth drive translates the second detector in the tangential direction.

4. The gamma camera of claim 1 wherein the radiation is at least one of emission radiation and transmission radiation.

5. The gamma camera of claim 1 wherein the first direction is a radial direction and the second direction is a tangential direction.

6. The gamma camera of claim 1 wherein the first relative angular orientation is a 120 degree orientation and the second relative angular orientation is an orthogonal orientation.

7. The gamma camera of claim 1 wherein the first relative angular orientation is a 180 degree orientation and the second relative angular orientation is an orthogonal orientation.

8. The gamma camera of claim 7 wherein the first and second detectors are selectively rotatable about the examination region in at least first, second, and third relative angular orientations, said third relative angular orientation being a 120 orientation.

9. A gamma camera comprising:
    first and second radiation sensitive detectors for detecting radiation indicative of radionuclide decays, the first and second detectors being selectively rotatable about an axis of rotation, the first detector being selectively rotatable about an axis of rotation disposed in the examination region in relation to the second detector such that the detectors are selectively positionable in at least first and second relative angular orientations for rotation about the examination region;
    a tangential drive operatively connected to the first detector;
    a radial drive operatively connected to the first detector;
    a tangential drive operatively connected to the second detector;
    a radial drive operatively connected to the second detector.

10. The gamma camera of claim 9 wherein the first and second relative angular orientations are a 120 degree orientation and an orthogonal orientation.

11. The gamma camera of claim 9 including rotational drive means for rotating the first and second detectors about the examination region.

12. A gamma camera comprising:
    first detector means for detecting radiation from an examination region;
    second detector means for detecting radiation from the examination region;
    means for translating the first detector in a first direction and in a second direction;
    means for translating the second detector in the first direction and in the second direction;
    wherein the second detector is translatable independently of the first detector and wherein the first detector is selectively rotatable about an axis of rotation with respect to the second detector such that the relative angular orientation of the detectors is selectively variable, and wherein the first and second detectors are selectively rotatable about the axis of rotation is at least first and second relative angular orientations.

13. The gamma camera of claim 12 including means for translating the first detector includes means for translating the first detector in a tangential direction and means for translating the first detector in a radial direction.

* * * * *